(12) United States Patent
Gaspard et al.

(10) Patent No.: US 8,116,838 B2
(45) Date of Patent: Feb. 14, 2012

(54) MEDICAL DEVICE FOR DIAGNOSING PRESSURE ULCERS

(75) Inventors: Sanna Gaspard, Pittsburgh, PA (US); Mel Siegel, Pittsburgh, PA (US); Todd M. Przybycien, Pittsburgh, PA (US); James F. Antaki, Allison Park, PA (US); David M. Brienza, Allison Park, PA (US); Mark B. Friedman, Pittsburgh, PA (US)

(73) Assignee: Carnegie Mellon University, Pittsburgh, PA (US)

(*) Notice: Subject to any disclaimer, the term of this patent is extended or adjusted under 35 U.S.C. 154(b) by 697 days.

(21) Appl. No.: 12/324,445

(22) Filed: Nov. 26, 2008

(65) Prior Publication Data

US 2009/0234206 A1    Sep. 17, 2009

Related U.S. Application Data

(60) Provisional application No. 61/004,435, filed on Nov. 27, 2007.

(51) Int. Cl.
*A61B 5/1455* (2006.01)
*A61B 5/103* (2006.01)

(52) U.S. Cl. .......... 600/322; 600/476; 600/323

(58) Field of Classification Search .......... 600/322–323, 600/355, 407, 490, 587, 368, 483, 300, 476; 606/9, 194; 382/124–126
See application file for complete search history.

(56) References Cited

U.S. PATENT DOCUMENTS

| | | | | |
|---|---|---|---|---|
| 5,088,817 A | * | 2/1992 | Igaki et al. | 356/71 |
| 5,623,933 A | * | 4/1997 | Amano et al. | 600/500 |
| 6,070,092 A | | 5/2000 | Kazama et al. | |
| 6,631,288 B1 | | 10/2003 | Bain et al. | |
| 6,808,497 B2 | * | 10/2004 | Ogura et al. | 600/490 |
| 7,155,273 B2 | | 12/2006 | Taylor | |
| 2005/0165284 A1 | | 7/2005 | Gefen | |
| 2006/0008128 A1 | * | 1/2006 | Setlak et al. | 382/124 |
| 2007/0276261 A1 | * | 11/2007 | Banet et al. | 600/481 |
| 2008/0146906 A1 | * | 6/2008 | Baker et al. | 600/407 |
| 2009/0299349 A1 | * | 12/2009 | Kubota et al. | 606/9 |

OTHER PUBLICATIONS

Gaspard et al., "Skin-Color-Compensated Colorimeter for Detection of Classification of Pressure Ulcers," IEEE Int. Instrum. and Meas. Tech. Conf., May 2008.

Quan et al., "Relationship between depth of a target in a turbid medium and fluorescence measured by a variable-aperture method," Optics Letters, vol. 27, No. 2, Jan. 2002.

Zhu et al., "Effect of fiber optic probe geometry on depth-resolved fluorescence measurements from epitheliam tissues . . . ," J. of Biomedical Optics 8(2), 237-247, Apr. 2003.

(Continued)

*Primary Examiner* — Long V. Le
*Assistant Examiner* — Lawrence Laryea
(74) *Attorney, Agent, or Firm* — K&L Gates LLP (57) ABSTRACT

Medical device or instrument for diagnosing pressure ulcers using optical reflectance spectroscopy. The device may comprise a tip and a controller. The tip is pressed against the skin of the patient and collects the optical reflectance data. The controller processes the data to determine whether there exists a pressure ulcer and, if there is one, its depth. The tip may also include a pressure sensor for sensing the pressure at which the tip is applied to the patient's skin.

56 Claims, 5 Drawing Sheets

OTHER PUBLICATIONS

Arifler et al., "Reflectance spectroscopy for diagnosis of epithelial precancer . . . ," Applied Optics, vol. 44, No. 20, Jul. 2005.

Feather et al., "A portable reflectometer for rapid quantification of cutaneous haemoglobin and melanin," Phys. Med. Biol., 1988, vol. 33, No. 6, 711-722.

Thomas, "Prevention and treatment of pressure ulcers: What works? What doesn't," Cleveland Clinic Journal of Medicine, vol. 68, No. 8, Aug. 2001.

Zanca, "Exploring Methods to Improve Pressure Ulcer Detection: Spectroscopic Assessment of the Blanche Response," Ph.D. Thesis, Univ. of Pittsburgh, 2006.

Jonsson, "New Sensor Design Made To Discriminate Between Tissue Blood Flow at Differential Tissue Depths at theSacral Area," 2006.

Gaspard et al., "Skin-color-compensated colorimeter for detection and classification of Pressure Ulcers," IEEE Int'l Instrumentation and Measurement Tech. Conf., May 2008.

Quan et al., "Relationship between depth of a targe in a turbid medium and fluorescence measured by a variable-aperature method," Optical Letters, vol. 27, No. 2, Jan. 2002.

Zhu et al., "Effect of fiber optic probe geometry on depth-resolved fluorescence measuments from epithelial tissues," J. of Biomedical Optics 8(2), Apr. 2003.

Arifler et al., "Reflectance spectroscopy for diagnosis of epithelial caner . . . ," Applied Optics, vol. 44, No. 20, Jul. 2005.

Feather et al., "A portable reflectometer for the rapid quantification of cutaneous haemoglobin and melanin," Phys. Med. Biol., vol. 33, No. 6, 1998.

D.R. Thomas, "Prevention and Treatment of Pressure Ulcers: What works? What doesn't?" Cleveland Clinic J. of Medicine, vol. 68, Aug. 2001.

* cited by examiner

MEDICAL DEVICE FOR DIAGNOSING PRESSURE ULCERS

PRIORITY CLAIM

The present application claims priority to U.S. provisional patent application Ser. No. 61/004,435, entitled "An Early Stage/Grade Pressure Ulcer Diagnostic Tool for Darkly Pigmented Skin," filed Nov. 27, 2007, which is incorporated herein by reference in its entirety.

STATEMENT REGARDING FEDERALLY SPONSORED RESEARCH AND DEVELOPMENT

This invention was made with government support under NIH No. 3R01HD041490-05S1. The government has certain rights in this invention.

BACKGROUND

Pressure ulcers (PUs), also known as bedsores, develop at the boney prominences of the body (e.g., heel, elbow, shoulder bones, sacrum). Currently, PU prevention is one of the greatest challenges facing caregivers, hospitals, and long term care facilities. PUs occur most frequently in institutionalized, community-dwellings and nursing homes for older adults, where they are a serious problem that can lead to sepsis and death. In nursing homes, PUs represent a significant problem for residents (in terms of morbidity, pain, and reduced quality of life) and for facilities (in terms of staffing and costs of care). Once a PU develops, it is costly and extremely difficult to heal. They are very resistant to known medical therapy and, unlike acute wounds, PUs do not proceed through an orderly and timely process of healing to reduce anatomical or functional integrity. PUs cost the US health care system approximately $1.3 billion every year. The prevalence of PUs ranges from 10-17% in acute care, 0-29% in home care, and 2.3-28% in institutional long-term care (LTC). The cost to heal a complex, full-thickness PU in 2006 was as much as $70,000; the cost for a less serious PU may range from $2000 to $30,000.

The development of PUs often is viewed as negligent care by a healthcare provider or a health system. Litigation stemming from PU development and negligence is high in the US despite the fact that PU incidence is monitored and preventative measures are mandated by the government. Typical PU awards in the US range from $5,000 to $82 million, with the median award approximately $250,000. PU prevention and litigation is also a large problem in Europe.

Currently, the early diagnosis of a PU is conducted using visual and tactile investigation of the skin. The standard tactile tool used clinically is the blanch test. The blanch test involves applying gentle pressure to the skin to observe the whitening or blanching of the skin. A blanching area of reddened skin indicates healthy tissue structure and perfusion. A non-blanching area of redness is diagnosed as a stage I PU. To the inventors' knowledge, all available commercial instruments designed to measure PUs are analytical instruments intended for experimental laboratory use only. Analytical experimental devices that shine light onto the skin and collect the light reflected back to identify or determine different properties of the skin (e.g. erythema and melanin content) have been designed. Analytical commercial narrow-band reflectance instruments that can be applied to the diagnosis of stage-I PUs function by utilizing erythema/melanin indices to identify erythema across individuals with varying skin pigmentation are known. Although these devices can detect erythema in spite of skin pigmentation, they have limited utility as bedside clinical tools because they are an expensive alternative to the manual blanch test, they are large and bulky for a bedside device, and they are not simple to use for an untrained professional. Rather, they are specifically designed for cosmetology/dermatology experimental research, where quantification of experimentally induced color changes is widely performed.

Portable devices that measure non-blanchable erythema or the microcirculation properties of the skin related to pressure ulcer development are known, including U.S. Pat. No. 6,631,288 ("the '288 patent") and U.S. Pat. No. 7,155,273 ("the '273 patent"). The devices described in these patents analyze reflected light to yield a diagnosis. They also contain varying components for applying pressure to the skin to observe blanching. The '288 patent utilizes a sliding probe that enables the reflectance data to be analyzed to monitor transient microcirculation (refill time) after blanching to infer the progression of the pressure ulcer. The '273 patent includes a specialized probe that simultaneously compares damaged and healthy tissue to get a personalized baseline for diagnosis. A major limitation of these patented designs is that the specialized probe depends on the user's skill level and ability to visually identify (the current subjective method of PU identification) the size and location of the stage I pressure ulcer (in light and dark skin), so that the probe can either be run along the length of the PU for microcirculation analysis and PU diagnosis or placed along the perimeter of the PU for simultaneous healthy and diseased tissue analysis and subsequent PU diagnosis. To the inventor's knowledge, neither of these patented designs has been successfully tested on humans or currently exist as commercial devices.

SUMMARY

In one general aspect, the present invention is directed to a device for diagnosing pressure ulcers (PUs) in patients using optical reflectance spectroscopy. According to one embodiment, the device comprises a tip and a processor-based controller. The tip is used to press against skin of the patient in the measurement region or testing area of the patient. The tip comprises an optical system for collecting the optical reflectance data, and the processor-based controller analyzes the optical reflectance data to determine whether there exists a PU in the measurement region of the patient. The optical system may comprise two or more photodetectors and an emitter assembly. The emitter assembly comprises two or more light sources for emitting light energy toward the skin of the subject, and the two or more photodetectors sense reflected light energy that is emitted from the emitter assembly and reflected by the skin of the measurement region. The tip also may comprise one or more pressure sensors for sensing the pressure at which the tip is applied by a user of the device to the skin of the subject.

The processor-based controller is in communication with the emitter assembly, photodetectors, and the pressure sensor (s), and is programmed to determine whether a PU is present in the measurement region based on input from the photodetectors and the pressure sensor(s). The controller is also programmed to detect the skin layer depth of the pressure ulcer when one is detected.

According to various implementations, the tip is concave. In addition, the controller may determine whether a pressure ulcer is present in the measurement region by calculating at least one of the following: (i) relative or absolute concentration levels of oxyhemoglobin, melanin, and deoxyhemoglobin at different skin layer depths of the measurement region at both a first pressure range and a second pressure range for the tip against the skin as measured by the pressure sensor(s); and (ii) a rate of change of blood concentration and/or oxygen saturation in the measurement region based on input from the photodetectors during a time period either prior or post application of gentle pressure. The device also may comprise a user interface in communication with the controller that (i) visually indicates to a user of the device whether a pressure ulcer was detected in the measurement region and (ii) visually indicates to the user the other measured properties of the skin in the measurement area. The user interface may also visually indicate to the user the applied pressure and provide operational instructions. In addition, the device may comprise a wireless transceiver in communication with the controller that transmits wireless data indicative of whether a pressure ulcer is detected and other measured properties of the skin to a remote computer system. The device may also include an audio output that outputs audio utterances that are captured by a voice-assisted care system, for example.

In addition, the device may comprise a detachable, flexible, non-transmissive skirt that surrounds the tip and blocks ambient light energy from the photodetectors. The photodetectors may comprise a first group that is a first distance from the emitter assembly and a second group that is a second, greater distance from the emitter assembly. The device may also include other groups of photodetectors that are located at other distances from the emitter assembly. By using photodetectors that are of different distances from the emitter assembly, the controller can determine the depth of the PU if one is detected.

Embodiments of the present invention provide numerous advantages over prior art techniques for diagnosing PUs. Devices of the present invention are likely to be more accurate than the standard, manual blanch test currently widely in the healthcare industry, and in particular, more accurate for people with darkly pigmented skin. In addition, the device in various embodiments can detect the depth level of a PU. Consequently, PUs can be detected at early stages in their development and treatments can be determined based on the depth of the PU. Additionally, the device in various embodiments is easy to use and is inexpensive in comparison to prior art erythema detection devices.

These and other benefits of the present invention will be apparent from the description below.

FIGURES

Various embodiments of the present invention are described herein by way of example in conjunction with the following figures, wherein.

DESCRIPTION

Figures 1, 3, 4:
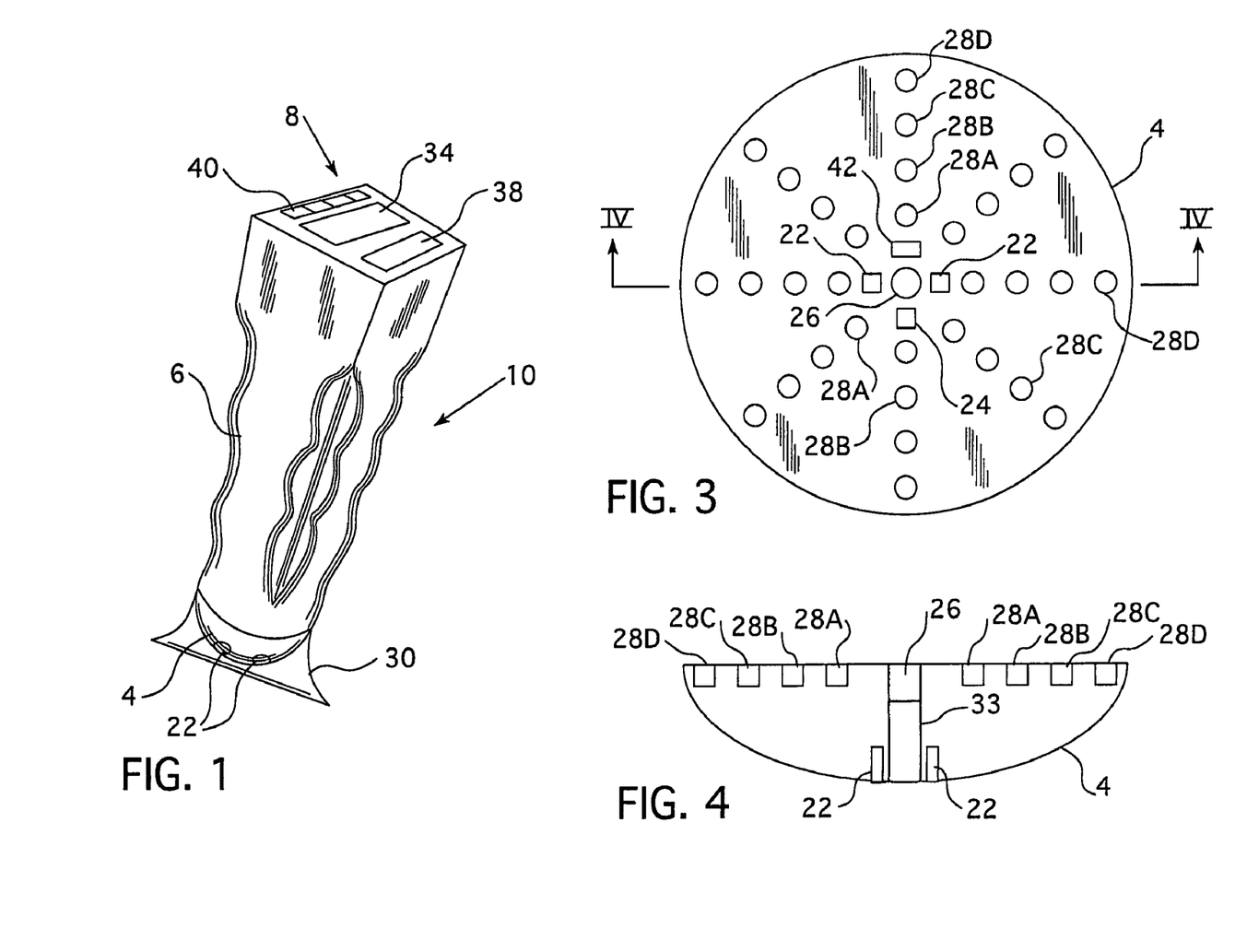
FIGS. 1 and 6 are diagrams of handheld devices for diagnosing pressure ulcers (PUs) according to various embodiments of the present invention.
FIGS. 3-5 are diagrams of the tip of the device according to various embodiments of the present invention.

The present invention is directed, in various embodiments, to a medical device or instrument that can be used to diagnose pressure ulcers (PUs) in subjects, such as human patients, using optical reflectance spectroscopy. FIG. 1 illustrates a handheld device 10 according to one embodiment of the present invention. The device 10 detects change in the relative or absolute concentration of oxyhemoglobin (oxyHb), deoxyhemoblobin (deoxyHb), and melanin in the region of the patient's body ("the measurement region") to which the device 10 is applied. As shown in the embodiment of FIG. 1, the handheld device 10 may include a tip 4, a housing 6, and a user interface 8. In operation, a user of the device 10 may grip the housing 6 and apply the tip 4 with varying degrees of pressure to an area of the patient's skin. As described further below, the tip 4 may comprise an optical system and one or more pressure sensors. The optical system transmits light energy toward the skin and detects the reflected light energy. This process is repeated for varying levels of pressure applied by the tip 4 to the patient's skin, as measured by the pressure sensor(s). Based on the reflected light detected by the optical system and the pressure sensor data, a processor-based controller, which may be located in the housing 6 in the embodiment of FIG. 1, determines whether there is a PU in the testing area or measurement region that the device 10 was applied to the patient and, if there is a PU, the skin layer depth of the PU in the measurement region. The controller may also gather data on additional measured properties of the skin and make a determination as to whether those properties are indicative of healthy or diseased tissue. The output from the determination by the controller may be displayed on the user interface 8. The devise may also be able to communicate with the user to indicate how much pressure the user is applying and when to apply pressure.

Figure 2:
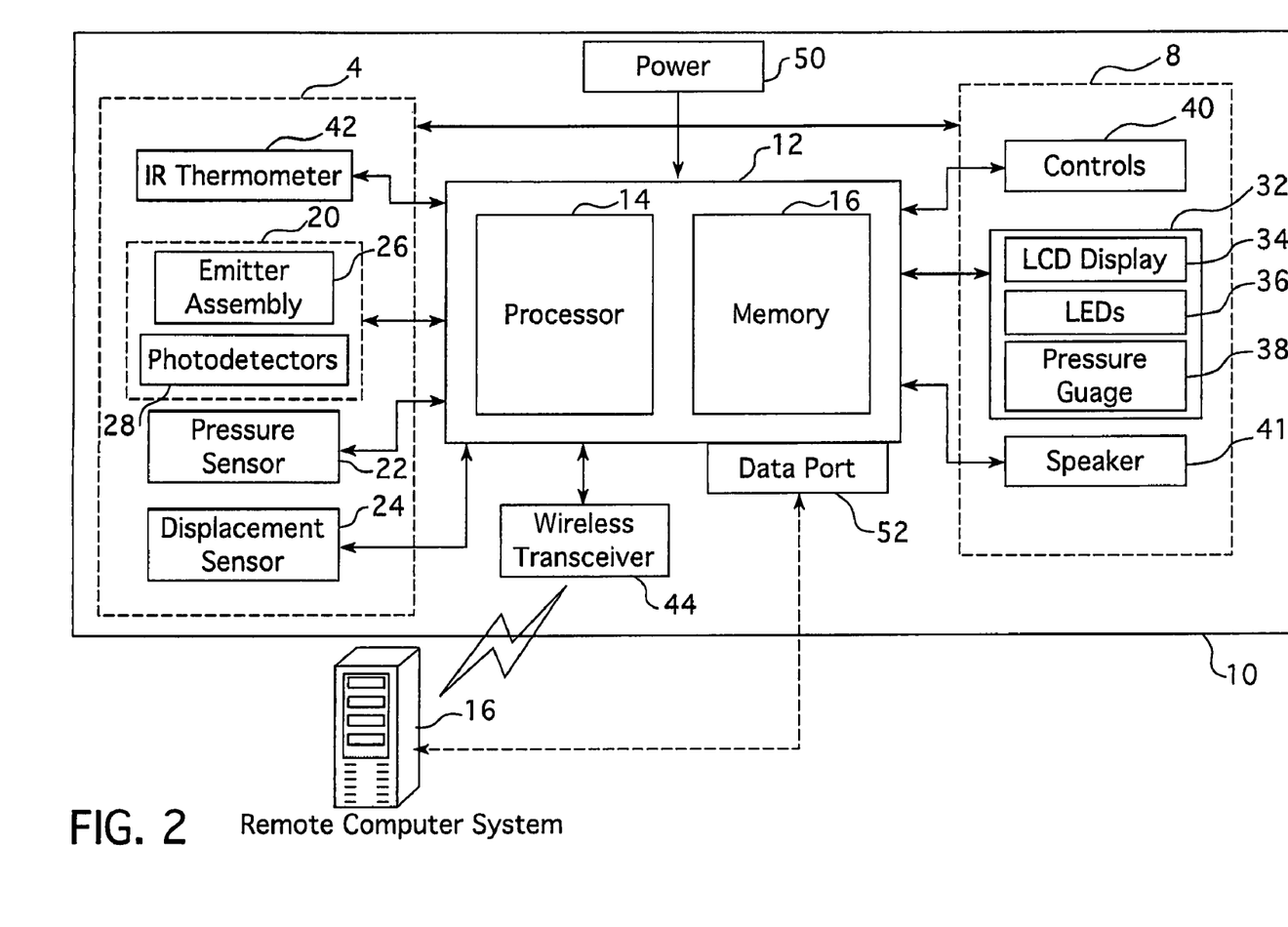
FIG. 2 is a block diagram of the device of FIG. 1 according to various embodiments of the present invention.

FIG. 2 is a block diagram of the device 10 according to various embodiments. As shown in FIG. 2, the device 10 includes the processor-based controller 12. The controller 12 may be, for example, a microcontroller comprising a processing core (or processor) 14 and a memory 16. The memory 16 may comprise ROM for program storage, read-write memory for storing data, and flash memory for permanent data storage. In one embodiment, the controller 12 may be implemented as a computer system-on-a-chip, including an integrated processor core 14 and memory 16. In other embodiments, the controller 12 may comprise discrete components, such as discrete processor(s) 14 and memory units. The controller 12 also may comprise analog-to-digital converters (ADC) and digital-to-analog converters (DAC) that convert analog signals to digital signals and digital signals to analog signals, as the case may be. The ACDs and DACs may be integrated into the microcontroller or may be discrete components, and are not shown in FIG. 2 for the sake of simplicity.

The device 10, according to various embodiments, may diagnose PUs based on inputs from an optical system 20 and one or more pressure sensors 22. The device 10 may also determine the firmness (or consistency or turgor) of the patient's skin based on input from a displacement sensor 24. The components 20, 22, 24 may be located in the tip 4 of the device 10 (see, for example, FIG. 1). The optical system 20 may comprise an emitter assembly 26 and a plurality of photodetectors 28. In one embodiment, the emitter assembly 26 may comprise a number of discrete wavelength-band light sources, such as light emitting diodes (LEDs), laser diodes, etc. The center wavelengths for the light sources preferably are different and are selected to yield signal vectors with elements that overlap the distinguishing spectral features of oxyHb, deoxyHb, and melanin. In various embodiments, the emitter assembly 26 may include several co-located light sources that emit light energy in the visible spectrum (VIS) and several light sources that emit light energy in the infrared (IR) spectrum.

The photodetectors 28 may comprise any suitable light energy detecting devices, including, for example, photodiodes, reverse-biased LEDs, phototransistors, etc. In one embodiment, as shown in FIG. 3, the emitter assembly 26 may be located in the center of the tip 4 with a number of photodetectors 28 distributed concentrically around the emitter assembly 26 at different radial distances from the emitter assembly 26. For example, with reference to FIG. 3, the first group of concentric photodetectors 28A is closer radially to the emitter assembly 26 that the second group of concentric photodetectors 28B, and so on. As described further below, the further a photodetector 28 is positioned from the emitter assembly 26, the deeper the relative or absolute concentration levels of oxyHb, deoxyHb, and melanin can be detected so that PUs at different skin layer depths of the patient can be detected. Accordingly, the photodetectors 28D can detect deeper PUs than the photodetectors 28C, and so on.

In the example of FIG. 3, each concentric group of photodetectors 28A-D comprises the same number of photodetectors. In other embodiments, the concentric groups may comprise different numbers of photodetectors. In particular, there may be room for additional circumferential photodetectors at the outer concentric groups. In addition, the photodetectors 28A-D may have different sizes, with the larger photodetectors collecting more light energy. In particular, the outer concentric groups of photodetectors (e.g., photodetectors 28D) may utilize larger photodetectors than the inner groups (e.g., photodetectors 28A). Using larger photodetectors may assist in collecting light energy reflected from deeper skin layers.

The emitter assembly 26 may sequentially emit pulsed light energy at the specific wavelength bands of the different light sources, and the pulses may be synchronized with the photodetectors 28 so that the photodetectors 28 can collect the reflected light from the skin tissue layers of the measurement region at the corresponding wavelength/frequency. The photodetectors 28 collect the reflected light at the corresponding wavelengths/frequencies over time for each light source of the emitter assembly 26 at wavelengths/frequencies specific to oxyHb, deoxyHb, and melanin. Based on the optical reflectance signals from the photodetectors 28, the controller 12 determines the depth at which the light is collected (based on the distance of the photodetector 28 from the emitter 26) and determines the relative or absolute concentration of oxyHb, deoxyHb, and/or melanin at each depth level. In various embodiments, the controller 12 may also calculate metabolism based on the reflectance data for the various skin layers.

The reflectance signals can be collected at two or more compression levels (e.g., light and gentle compression), and the controller 12 can compare the change in the relative or absolute concentration levels at the different compression levels to determine at what skin layer depth blanching (or non-blanching) is occurring. Non-blanching is indicative of tissue damage that may be a PU. Prior circuits for the optical system 20 are not shown in FIG. 2 for the sake of simplicity, and persons of ordinary skill in the art understand how to make and use such drive circuits.

As shown in FIG. 4, the tip may comprise an optically non-transmissive shroud 33 around the light sources of the emitter assembly 26 that effectively blocks light from the emitter assembly 26 from directly impinging on the photodetectors 28. That way, the photodetectors 28 are effectively optically isolated from the emitter assembly 26 so that the photodetectors 28 primarily detect light energy reflected from the skin and not light energy from the emitter assembly.

The tip 4 may also include one or more pressure sensors 22, as shown in FIG. 4, preferably embedded in the tip 4 or otherwise positioned at the exterior of the tip 4. In various embodiments, the pressure sensors 22 may comprise microelectromechanical systems (MEMS) pressure sensors 22. The pressure sensors 22 may sense the pressure at which the tip 4 is applied to the skin (or body) of the patient. The outputs of the pressure sensors 22 may be coupled to the controller 12, which uses the pressure data, in conjunction with the spectroscopy data from the optical system 20, to determine whether there exists a PU in the measurement region. The user interface 8 may also output an indication of the pressure applied, as described further below. Based on the pressure reading output, the user can adjust the magnitude of the applied pressure to within the required ranges for the various compression levels used in the diagnosis process. The visual display of the applied pressure aids in standardizing the pressure application between users and standardizes the amount of expected deformation during compression for data analysis within a specific range. The user interface 8, as described further below, may include other user feedback indicators regarding the pressure application levels.

In various embodiments, the tip 4 may also include a displacement sensor 24 that measures the firmness of the patient's skin. Any suitable displacement sensor may be used, including micro-, non-invasive, tactile displacement sensors 24. Based on the output signal from the displacement sensor 24, the controller 12 may calculate the firmness of the skin in the measurement region, and the output of this calculation may be displayed on the user interface (e.g., on the LCD display 34). In another embodiment, the tip 4 may be spring-loaded so that the vertical force applied by the user can be used to determine the displacement of the skin and further analyzed by the device 10 to determine skin firmness.

The tip 4 preferably comprises an optically transmissive material having a reflective index that is the same as or similar to the reflective index of the medium in which the device 10 is used, such as air. For example, the tip 4 may be made of plastic or glass, or any suitable material that is wipeable. The tip 4 preferably is curved (or concave), as shown in the example of FIG. 1, to facilitate accurate collection of the reflected light from curved surfaces of the body, like the heel. PUs at the heels have the highest incidence rate. A concave tip 4 also aids in applying uniform force/pressure to the skin when the device 10 is placed in direct contact with the skin and the user applies force. Uniform pressure is preferable because it allows blanching to be measured more accurately.

As shown in FIG. 1, the device 10 may also include a skirt 30 that surrounds the tip 4. The skirt 30 preferably comprises an optically non-transmissive material that effectively blocks ambient light from reaching the photodetectors 28 when the device 10 is in use. The skirt 30 preferably comprises a flexible material, such as plastic or rubber, that flares out along its sides to form a substantially closed and sealed enclosure around the tip 4 when the device 10 is contacted against the patient, given the possible contours of the patient's body where the device 10 is applied. The skirt 30 also preferably extends past the tip and is flexible so that it will form the enclosed area around the tip 4 when the device 10 is pressed against a body region of the patient. In addition, the skirt 30 preferably is releaseably connected to the body 6 or other part of the device 10, such as by an adhesive, Velcro hooks and loops, an elastic fit, a releasable snap-fit, or any other suitable connection means, so that the skirt 30 can be removed and disposed of after each use and replaced with a new one to reduce the transmission of biological matter between patients when the device 10 is used on successive patients. The tip 4 may also be cleaned with an anti-bacterial wipe after each use to reduce further the transmission of biological matter between patients.

Returning to FIGS. 1 and 2, the user interface 8 may be located, in various embodiments, at the opposite end of the housing 6 from the tip 4. The user interface 8 may include visual indicators 32 that provide feedback to the user. For example, in various embodiments, the user interface 8 may comprise a LCD or other type of alphanumeric display 34, one or more output LEDs 36, and a digital or analog pressure gauge 38. The LCD display 34 may provide the user with information depending on the mode of operation of the device 10. For example, the LCD display 34 may provide a visual indication of whether a PU is detected and, if so, the skin layer depth of the PU. For example, if no PU is detected, the LCD display 34 may display a message that indicates that no PU is detected. Conversely, if a PU is detected, the message might say "PU detected at depth x," or something to that effect or display the information pictorially (or graphically). The LCD display 34 may also display or indicate the skin temperature (as measured by the optional thermometer 42 described below) or the skin firmness (as determined based on the output from the displacement sensor 24) when the user selects these other operational modes for the device 10.

The pressure gauge 38, which may be a digital LED or LCD display or an analog display, for example, provides a visual indication of the pressure applied by the user to the patient's skin, as sensed by the pressure sensor(s) 22 and output to the pressure gauge 38 by the controller 12. According to various embodiments, in operation, the user is first to apply light (or little) pressure with the device 10 to the patient's skin while the device 10 collects the reflectance data in this pressure range. The various light sources of the emitter assembly 26 may be activated sequentially during this stage and the photodetectors 28 collect the reflectance data for each separate light source. Then the user applies slightly greater (or gentle) pressure while the device 10 collects the reflectance data in this pressure range. The pressure gauge 38 may indicate the pressure so that the user can determine whether it is in the desired pressure range for each stage. The controller 12 uses the reflectance data from each pressure level to determine the existence of a PU. The light (or low) pressure data serves as a baseline measurement to compare with the gentle (or high) pressure data. The user may have to maintain the pressure for 2 to 30 seconds for each pressure stage according to various embodiments in order for the necessary spectroscopic data to be collected. The device 10 preferably is used to collect optical data on the skin at various pressure levels at a suspected pressure ulcer location and at an anatomically similar healthy site. The optical data on the healthy site preferably serves as a baseline measurement for comparison.

In various embodiments, the user interface 8 comprises at least three output LEDs 36. In various embodiments, the LEDs may output different color light energy and may to indicate different operating conditions. For example, when the user first turns on the device, a first LED 36 (e.g., a green LED) may be lit to indicate/inform the user that the device is ready for use and can be placed in contact with the patient's skin. If the applied pressure is outside of the desired range (e.g., outside the light (or low) pressure range), the first LED 36 may blink to alert the user. In addition or alternatively, an audio indicator, such as an alarm or chime, may be output by a speaker 41 indicate that the pressure is outside of the desired range.

In various embodiments, once the reflectance data for the low pressure stage is collected, a second LED 36 (e.g., a yellow LED) may be lit to inform or indicate to the user that more pressure should be applied so that light reflectance data for the high pressure stage may be collected. Again, if the applied pressure is outside of the desired pressure range for the high-pressure light reflectance data collection, the speaker 41 and/or one of the LEDs 36 may provide an indicator to the user of this condition. Once the high pressure and blood reflow data is collected, the third LED 36 (e.g., a red LED) may be lit to indicate to the user that the device 10 can be removed from contact with the patient. The device 10 may not collect data unless the pressure is within the correct range. That is, the controller 12 may continuously monitor the pressure and, if the pressure is outside of the desired range, the controller 12 does not analyze the optical reflectance data collected while the pressure was outside of the desired pressure range. The process may be repeated for an anatomically similar healthy site, with the spectroscopic data from both sites (e.g., healthy and testing area) used to determine the existence of the PU at the testing area.

The user interface 8 may also include user controls 40, such as on and off button(s) and/or switches for turning the device 10 on and off. The user controls 40 may also include one or more controls for allowing the user to change the operation mode of the device 10. For example, using the user controls, the user could cycle through or otherwise select various operational modes of the device 10, including PU diagnosis, skin firmness determination (based on the displacement sensor 24), and skin temperature readings (based on the thermometer described below).

The device 10 may also comprise a thermometer 42 as shown in FIG. 2. The thermometer may be internal or external to the body 6 of the device 10 and allows temperature readings of the skin at the tested site of the patient. In various embodiments, the thermometer may be an IR thermometer or some other type of non-contact thermometer that measures the temperature of the measurement region of the patient. The temperature readings from the thermometer 42 may be displayed for the user on the user interface 8, such as on the LCD display 34. The controller 12 may control the IR thermometer 42 and the optical system 20 so that the IR energy from the IR thermometer 42 is not radiated when the optical system 20 is collecting the reflectance data.

In addition, the device 10 may include a wireless transceiver 44 as shown in FIG. 2. The wireless transceiver 44 may be discrete from the controller 12 or could be integrated into the controller 12. The wireless transceiver 44 may be used to communicate wirelessly with a remote computer system 46. The remote computer system 46 may store patient data and include electronic medical record keeping software. That way, the data collected by the device 10 can be transmitted directly to the electronic medical record keeping system, thereby avoiding the need to record the data on paper and then manually input into the system 46. The wireless transceiver 44 may communicate with the remote computer system 46 using any suitable wireless communication protocol, including, for example, IEEE 802.11 (Wi-Fi), IEEE 802.15 (Zigbee), IEEE 802.16 (WiMAX), Bluetooth, etc. In an embodiment where the device 10 includes such a wireless transceiver 44, the wireless transceiver 44 may transmit a patient ID and data from the PU diagnosis, which data may be stored in the remote computer system 46.

The speaker 41 may also output audible utterances that may be captured, recognized, and stored by a computerized voice-assisted care system (not shown). The utterances may include data or results from the PU diagnosis. An example computerized voice-assisted care system is the AccuNurse voice-assisted care system from Vocollect Healthcare Systems.

The device 10 may also comprise a power system 50 for supplying electrical power to the controller 12 and other components that require power, such as the optical system 20, the user interface 8, the IR thermometer 42, etc. The power system 50 may comprise, for example, a power source, such as one or more battery cells, and one more power converters for converting the power from the power source to the appropriate levels for the various components. The power source may include, for example, one or more rechargeable or disposable battery cells. In another embodiment, the power system 50 may receive power from an external source, such as an uninterruptible power supply, AC mains, etc.

The device 10 also may comprise a data port 52, such as a USB port, a FireWire port, a SCSI port, or any other suitable data port. The data port 52 allows the device 10 to be connected directly to the remote computer system 46 so that data from the diagnoses conducted by the device 10 can be downloaded directly to the remote computer system 46.

The memory 16 of the controller 12 may include code that is executed by the processor(s) 14. When executed, the code may cause the controller 12 to, among other things: (1) monitor user variability, including application pressure levels; (2) provide user feedback; (3) measure and determine the magnitude of the properties of the patient's skin tissue (including, e.g., melanin concentration, oxyHb and deoxyHb (both static (with pressure) and transient (between pressure levels)), skin firmness, skin temperature, metabolism, etc.) based on the inputs from the optical system 20, the pressure sensor 22, the displacement sensor 24, and/or the temperature sensor 42 to provide a diagnosis using a mathematical algorithm; and (4) output an accurate diagnosis based on the measured properties of the skin tissue. The controller 12 may output the results of the diagnosis to the user interface 8, the wireless transceiver 44, and/or the speaker 41 as described above. In particular, the controller 12 may use the optical reflectance data captured by the optical system 20 from both static pressure stages (e.g., light (or low) pressure and gentle (or high) pressure, as detected by the pressure sensor 22), to aid in the determination of the whether there exists a PU. The controller 12 may also utilize the optical reflectance data captured by the optical system 20 from the time period immediately after the application of the gentle pressure (transient pressure) to aid in the determination of whether there exists a PU. The data from this transient condition is indicative of the rate of blood return to the measurement region, which is related to whether the tissue of the measurement region is healing or progressing in severity.

Figure 5:
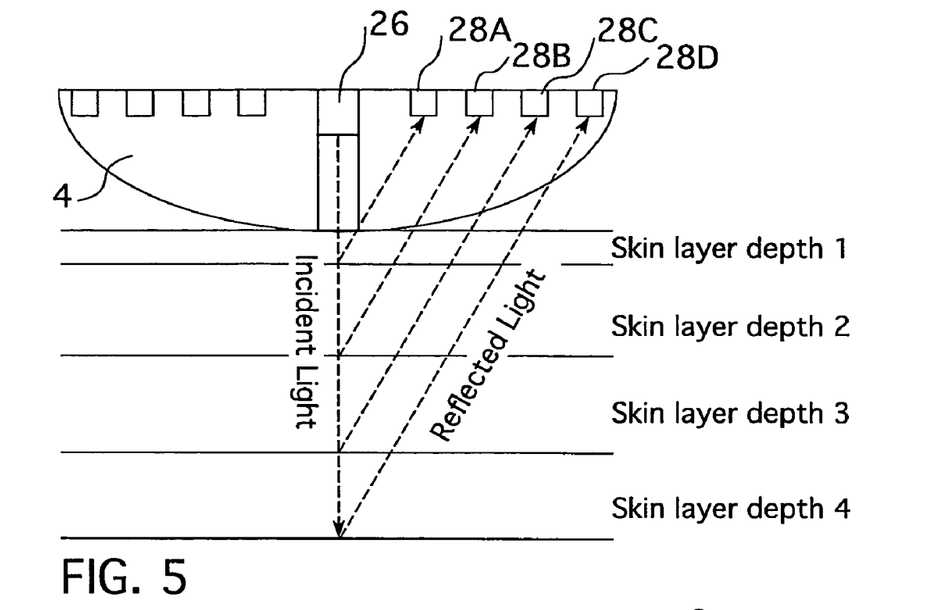

The controller 12 may be able to determine the depth of the PU (if one is detected) based on the optical reflectance data. Light from the deepest tissue layers of the measurement region of the patient are detected by the photodetectors 28 furthest from the emitter assembly 26, e.g., the photodetectors 28D in FIG. 3. With reference to FIG. 5, the photodetectors 28B detect light from deeper tissue layers that the inner photodetectors 28A, and the photodetectors 28C detect light from deeper tissue layers than photodetectors 28B, and so on.

The controller 12 may calculate the relative or absolute concentrations of oxyHb, deoxyHb, and melanin based on the optical reflectance data for both pressure stages and the transient pressure stage in order to detect whether there exists a PU in the measurement region of the patient's skin. According to various embodiments, the controller 12 may use a light propagation model, like a modified Kubelka-Munk theory, as the reflectance model when analyzing the optical reflectance data.

Figure 6:
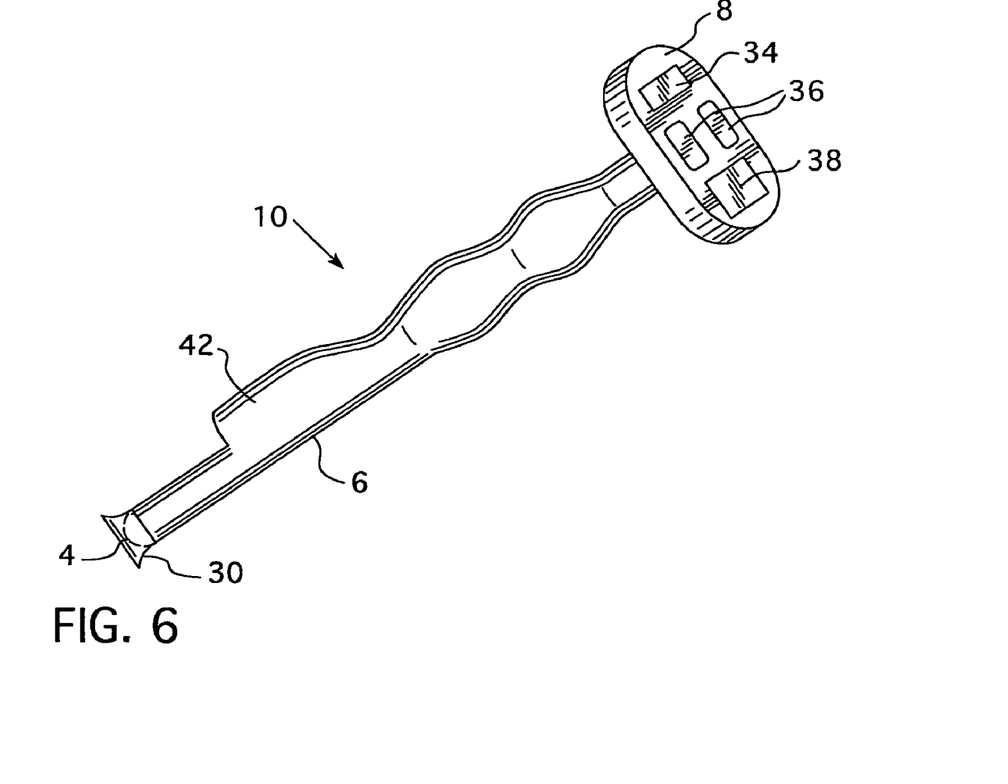

FIG. 6 shows another handheld embodiment of the device 10. The device 10 shown in FIG. 6 has a pen-grip configuration. Preferably, the pen-grip configured device 10 is approximately six inches long with a width of approximately 1.5 inch. In the illustrated embodiment, the user interface 8 is shaped as a flat disc with, for example, a 2.5 inch diameter. In addition, as shown in the example of FIG. 6, the IR thermometer 42 is positioned along the housing 6 in such an embodiment, although in other embodiments the IR thermometer 42 could be co-located in the tip 4.

Figure 7:
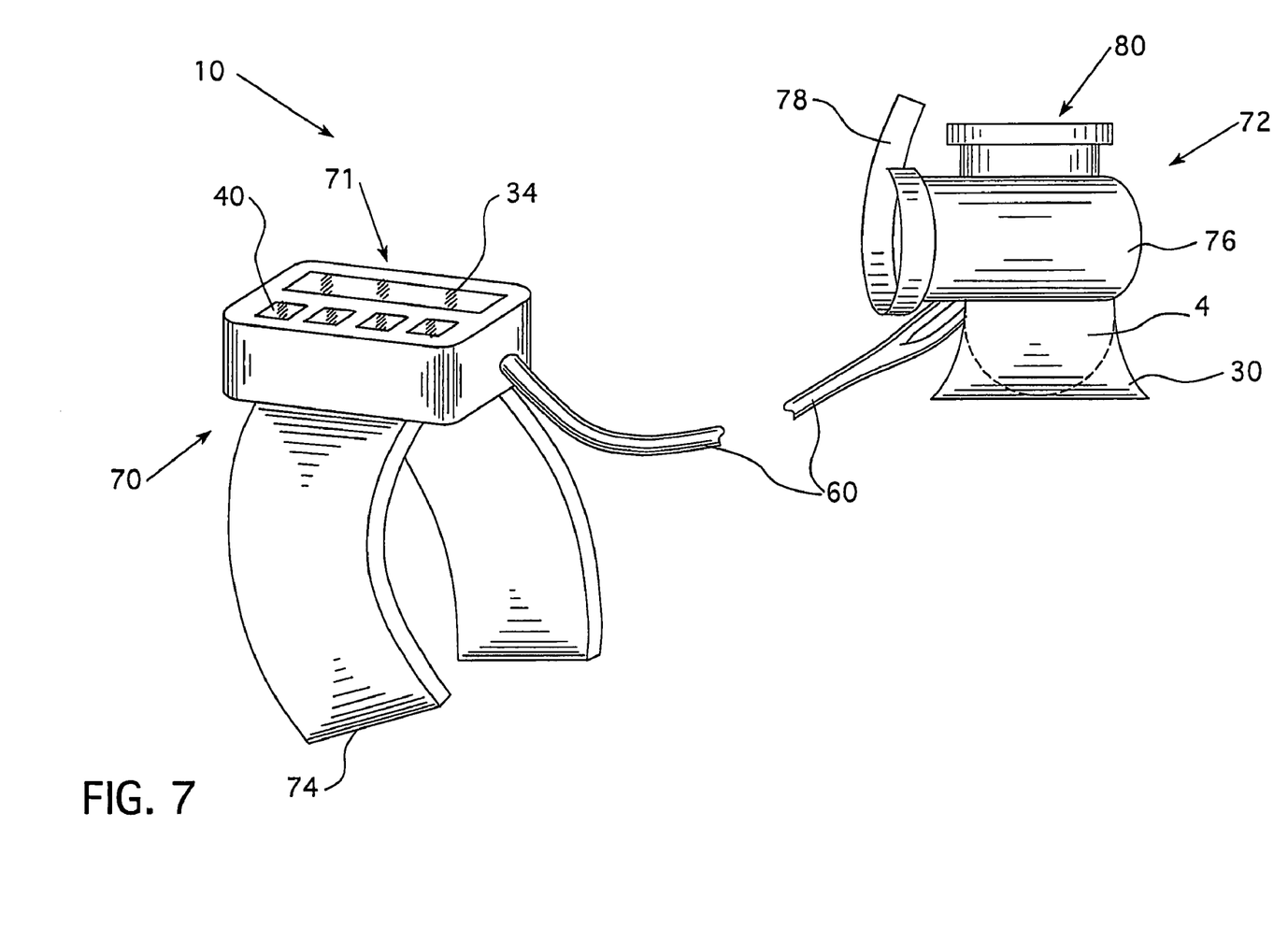
FIGS. 7 and 8 are diagrams of multi-component devices according to various embodiments of the present invention.

FIG. 7 shows a configuration of the device 10 that includes separate wrist and finger components 70, 72 that are connected by a life line 60 that houses the necessary optical fibers and electrical wires. In the illustrated embodiment, the wrist component 70 may comprise the controller 12 (not shown) and a first user interface 71. For example, the first user interface 71 may include the display 34 and the operational buttons 40. The wrist component 70 may be secured to the user's wrist via a Velcro or elastic strap 74, for example.

The finger component 72 includes, as shown in FIG. 7, a sleeve 76 in which the user can insert one of his/her fingers, preferably with a snug fit that prevents the finger from easily slipping out of the sleeve 76. The sleeve 76 may comprise a flexible material that adheres to the user's finger, and can be secured with a strap 78, which may be a Velcro strap.

The underside of the sleeve 76 comprises the tip 4, including the optical system 20, the pressure sensor(s) 22, the displacement sensor 24, and/or the IR thermometer 42. The finger component 72 may also include the skirt 30 around the tip 4. The upper side of the sleeve 76 may comprise a second user interface 80, which may include, for example, the pressure gauge 38 and/or the pressure user-feedback LEDs 36. In use, the user could, using his/her finger, place the finger compartment 72 on the testing area of the patient, with the tip 4 contacting the patient's skin. The user could apply pressure with their finger and monitor the pressure levels via the second under interface 80. The user could view the diagnosis on the first user interface 71.

In the embodiment of FIG. 7, according the various embodiments, the emitter assembly 26 and/or the photodetectors 28 may be located at the wrist component 70. In such an embodiment, the light energy may be carried to and from the tip 4 via fiber optic cables in the life line 60. The fiber optic cables may have different sizes (e.g., diameters), with larger cables carrying more light energy. Using larger fiber optic cables may assist in collecting light energy reflected from deeper skin layers.

Figure 8:
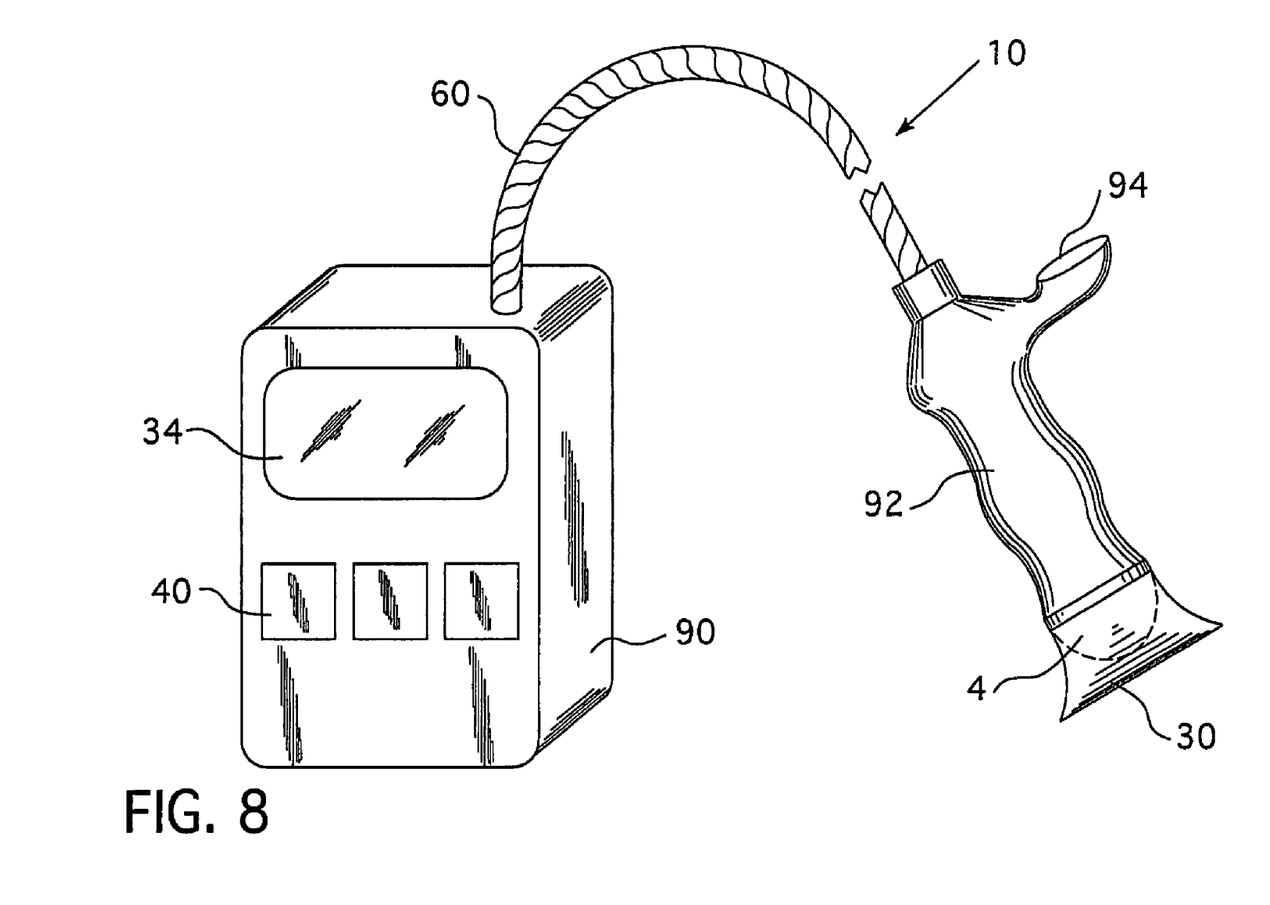

FIG. 8 provides illustrates yet another embodiment of the device 10. In this embodiment, the device 10 comprises a wearable component 90 and a hand-held probe 92 connected by a life line 60. The wearable component 90 may include a clip (not shown) that allows the user to attach or connect the wearable component 90 to their person or clothing, such as their belt. The wearable component 90 may comprise the controller 12 and a user interface comprising the LCD display 34 and the operational controls 40.

The probe 92 may comprise the tip 4 (with the optical system 20, the pressure sensor(s) 22, the displacement sensor 24, and/or the IR thermometer 42) and the skirt 30. The probe 92 may also include a user interface 94 that extrudes from the side of the probe 92. The probe user interface 94 may include, for example, the pressure gauge 38 and/or the LEDs 36. The probe 92 may be, for example, five inches long and three inches wide.

In the embodiment of FIG. 8, according the various embodiments, the emitter assembly 26 and/or the photodetectors 28 may be located at the wearable component 90. In such an embodiment, the light energy may be carried to and from the tip 4 via fiber optic cables in the life line 60. The fiber optic cables may have different sizes, with larger cables carrying more light energy.

Embodiments of the present invention provide numerous advantages over prior art techniques for diagnosing PUs. First, it is likely to be more accurate than the standard, manual blanch test. In particular, prototype testing shows that the embodiments of the device of the present invention can detect PUs in people with differently pigmented skin, including people with darkly pigmented skin. See S. Gaspard et al., "Skin-Color-Compensated Colorimeter for Detection and Classification of Pressure Ulcers," IEEE International Instrumentation and Measurement Technology Conference (2008), which is incorporated herein by reference in its entirety. The prior art manual blanch test is generally not effective at detecting PUs in people with darkly pigmented skin.

Second, the device 10, in various embodiments, can detect the depth level of a PU. Consequently, PU treatments for stage I PUs can be tailored to the severity and depth of the PU. Third, the device 10, in various embodiments, measures and analyzes additional physical properties of the skin relevant to clinicians for PU diagnosis and monitoring. Fourth, the device 10 in various embodiments, is easy to use and is inexpensive in comparison to prior art erythema detection devices.

The examples presented herein are intended to illustrate potential and specific implementations of the embodiments. It can be appreciated that the examples are intended primarily for purposes of illustration for those skilled in the art. No particular aspect or aspects of the examples is/are intended to limit the scope of the described embodiments.

It is to be understood that the figures and descriptions of the embodiments have been simplified to illustrate elements that are relevant for a clear understanding of the embodiments, while eliminating, for purposes of clarity, other elements well known in the art. Because such elements are well known in the art and because they do not facilitate a better understanding of the embodiments, a discussion of such elements is not provided herein.

In general, it will be apparent to one of ordinary skill in the art that at least some of the embodiments described herein may be implemented in many different embodiments of software, firmware and/or hardware. The software and firmware code may be executed by a processor or any other similar computing device. The software code or specialized control hardware, which may be used to implement embodiments, is not limiting.

In various embodiments disclosed herein, a single component may be replaced by multiple components and multiple components may be replaced by a single component to perform a given function or functions. Except where such substitution would not be operative, such substitution is within the intended scope of the embodiments.

While various embodiments have been described herein, it should be apparent that various modifications, alterations, and adaptations to those embodiments may occur to persons skilled in the art with attainment of at least some of the advantages. For example, different materials may be used than those described above for certain components. The disclosed embodiments are therefore intended to include all such modifications, alterations, and adaptations without departing from the scope of the embodiments as set forth herein.

What is claimed is:

1. A device for diagnosing pressure ulcers in a measurement region of a subject, the device comprising:
   a tip for pressing against skin in the measurement region of the subject;
   two or more photodetectors;
   an emitter assembly, comprising two or more light sources, for emitting light energy from the tip toward the skin of the subject, wherein the two or more photodetectors sense reflected light energy that is reflected by the skin of the measurement region;
   at least one pressure sensor for sensing the pressure at which the tip is applied to the skin of the subject; and
   a processor-based controller in communication with the two or more photodetectors and the at least one pressure sensor, wherein the controller is programmed to determine whether a pressure ulcer is present in the measurement region and, when a pressure ulcer is detected, to determine a skin layer depth of the pressure ulcer, based on input from the two or more photodetectors and the at least one pressure sensor.

2. The device of claim 1, wherein the tip is concave.

3. The device of claim 1, wherein the controller is for determining whether a pressure ulcer is present in the measurement region in part by calculating concentration levels of oxyhemoglobin, melanin, and deoxyhemglobin at different skin layer depths of the measurement region at both a first pressure range and a second pressure range for the tip against the skin as measured by the at least one pressure sensor.

4. The device of claim 3, wherein the controller is further for determining whether a pressure ulcer is present in the measurement region in part by calculating a rate of change of blood concentration in the measurement region based on input from the two or more photodetectors during a time period following application of pressure in the first pressure range.

5. The device of claim 3, wherein the controller is further for determining whether a pressure ulcer is present in the measurement region in part by calculating a rate of change of blood concentration in the measurement region based on input from the two or more photodetectors during a time period following application of pressure in the second pressure range.

6. The device of claim 3, further comprising at least one output indicator in communication with the controller, wherein the at least output indicator visually indicates to a user of the device whether a pressure ulcer was detected in the measurement region.

7. The device of claim 3, wherein the controller is further programmed to monitor the pressure at which a user applies the tip to the subject's skin.

8. The device of claim 7, further comprising:
   a display in communication with the controller for visually indicating to a user of the device whether a pressure ulcer was detected in the measurement region; and
   at least one visual indicator in communication with the controller for providing feedback to the user regarding the pressure at which the user is applying the tip to the subject's skin.

9. The device of claim 8, wherein the controller is programmed to determine whether to analyze input from the photodetectors based on the pressure at which the user is applying the tip to the subject's skin.

10. The device of claim 1, further comprising a wireless transceiver in communication with the controller, wherein the wireless transceiver transmits a wireless data signal indicative of whether a pressure ulcer was detected.

11. The device of claim 1, further comprising a detachable, flexible, non-transmissive skirt that surrounds the tip and blocks ambient light energy from the two or more photodetectors.

12. The device of claim 1, wherein the two or more photodetectors comprise a plurality of photodetectors that are positioned concentrically around the emitter assembly, such that a first group of the photodetectors are a first distance from the emitter assembly and a second group of the photodetectors are a second distance from the emitter assembly.

13. The device of claim 1, further comprising a thermometer for measuring a temperature of the skin in the measurement region, wherein the controller is in communication with the thermometer.

14. The device of claim 1, wherein the subject comprises a human.

15. The device of claim 1, further comprising a speaker in communication with the controller.

16. The device of claim 1, further comprising a pressure gauge in communication with the controller, wherein the pressure gauge indicates the pressure at which the tip is applied against the skin of the subject.

17. The device of claim 1, wherein the device comprises a body connected to the tip, and wherein the controller is housed in the body.

18. The device of claim 1, wherein the device comprises:
a first component that comprises the tip; and
a second component that comprises the controller, wherein the first component is connected to the second component by a lifeline.

19. The device of claim 18, wherein the first component is attachable to a finger of a user of the device.

20. The device of claim 19, wherein the second component is attachable to a wrist of the user.

21. The device of claim 18, wherein the second component includes a clip for attaching the second component to a user of the device.

22. The device of claim 18, wherein:
the first component comprises a pressure gauge; and
the second component comprises a LCD display.

23. The device of claim 1, further comprising a displacement sensor that is in communication with the controller.

24. The device of claim 1, wherein the light sources of the emitter assembly comprise at least one visible light source and at least one infrared light energy source.

25. The device of claim 1, wherein the light sources of the emitter assembly comprise at least one light emitting diode.

26. The device of claim 1, further comprising a data port, such that the device may be communicatively coupled to a remote computer system via the data port.

27. A device for diagnosing pressure ulcers in a measurement region of a subject, the device comprising:
a tip for pressing against skin in the measurement region of the subject, wherein the tip comprises:
a plurality of photodetectors;
an emitter assembly, comprising two or more light sources, for emitting light energy toward the skin of the subject, wherein the plurality of photodetectors sense reflected light energy that is emitted from the emitter assembly and reflected by the skin of the measurement region, wherein the plurality of photodetectors are positioned concentrically around the emitter assembly such that a first group of the photodetectors are a first distance from the emitter assembly and a second group of the photodetectors are a second distance from the emitter assembly; and
at least one pressure sensor for sensing the pressure at which the tip is applied to the skin of the subject; and
a processor-based controller in communication with the plurality of photodetectors and the at least one pressure sensor, wherein the controller is programmed to determine whether a pressure ulcer is present in the measurement region; and
a user interface in communication with the controller for displaying whether a pressure ulcer is detected in the measurement region.

28. The device of claim 27, wherein:
the controller is further programmed to determine a skin layer depth of the pressure ulcer, based on input from the two or more photodetectors and the at least one pressure sensor, when a pressure ulcer is detected; and
the user interface is for displaying the skin layer depth.

29. The device of claim 28, wherein the tip is concave.

30. The device of claim 29, wherein the controller is for determining whether a pressure ulcer is present in the measurement region in part by calculating concentration levels of oxyhemoglobin, melanin, and deoxyhemglobin at different skin layer depths of the measurement region at both a first pressure range and a second pressure range for the tip against the skin as measured by the at least one pressure sensor.

31. The device of claim 30, further comprising a detachable, flexible, non-transmissive skirt that surrounds the tip and blocks ambient light energy from the two or more photodetectors.

32. The device of claim 31, further comprising a thermometer for measuring a temperature of the skin in the measurement region, wherein the controller is in communication with the thermometer.

33. The device of claim 31, further comprising a pressure gauge in communication with the controller, wherein the pressure gauge indicates the pressure at which the tip is applied against the skin of the subject.

34. The device of claim 31, wherein the device comprises a body connected to the tip, and wherein the controller is housed in the body.

35. The device of claim 31, wherein the device comprises:
a first component that comprises the tip; and
a second component that comprises the controller, wherein the first component is connected to the second component by a lifeline.

36. The device of claim 35, wherein the first component is attachable to a finger of a user of the device.

37. The device of claim 36, wherein the second component is attachable to a wrist of the user.

38. The device of claim 35, wherein the second component includes a clip for attaching the second component to a user of the device.

39. The device of claim 35, wherein:
the first component comprises a pressure gauge; and
the second component comprises a LCD display.

40. A method of diagnosing pressure ulcers on a patient, the method comprising:
at a first site of the patient,
(i) applying a tip of a diagnostic device against the skin of the patient with a first pressure level and maintaining the first pressure level within a first pressure range for a first period of time, wherein the diagnostic device comprises:
two or more photodetectors;
an emitter assembly, comprising two or more light sources, for emitting light energy from the tip toward the skin of the subject, wherein the two or more photodetectors sense reflected light energy that is reflected by the skin of the measurement region; and at least one pressure sensor for sensing the pressure at which the tip is applied to the skin of the subject; and a processor-based controller in communication with the two or more photodetectors and the pressure sensor; and (ii) applying the tip of the diagnostic device against the skin of the patient with a second pressure level and maintaining the second pressure level within a second pressure range for a second period of time; and at a second site of the patient, repeating steps (i) and (ii).

41. The method of claim 40, wherein the first pressure range is less than the second pressure range.

42. The method of claim 40, further comprising displaying on a user interface of the device whether a pressure ulcer was detected at the first or second site.

43. The method of claim 42, further comprising displaying on the user interface a skin depth layer of the pressure ulcer when a pressure ulcer is detected.

44. The method of claim 43, further comprising displaying on the user interface the pressure at which the tip is being applied to the skin of the subject.

45. The method of claim 44, further comprising displaying on the user interface an indication of the skin temperature of the first or second site.

46. The method of claim 45, further comprising displaying on the user interface an indication of the skin firmness of the first or second site.

47. The method of claim 40, further comprising continuously monitoring the pressure at which the tip is being applied to the first or second site of the patient.

48. A device for diagnosing pressure ulcers in a measurement region of a subject, the device comprising:

a tip for pressing against skin in the measurement region of the subject;

two or more photodetectors;

an emitter assembly, comprising two or more light sources, for emitting light energy from the tip toward the skin of the subject, wherein the two or more photodetectors sense reflected light energy that is reflected by the skin of the measurement region;

at least one pressure sensor for sensing the pressure at which the tip is applied to the skin of the subject;

a displacement sensor;

a temperature sensor;

a processor-based controller in communication with the two or more photodetectors, the at least one pressure sensor, the displacement sensor, and the temperature sensor; and a display in communication with the controller.

49. The device of claim 48, wherein the controller is programmed to:

determine whether a pressure ulcer is present in the measurement region and, when a pressure ulcer is detected, to determine a skin layer depth of the pressure ulcer, based on input from the two or more photodetectors and the at least one pressure sensor;

determine skin firmness based on input from the displacement sensor; and determine skin temperature based on input from the temperature sensor.

50. The device of claim 49, wherein the controller is further programmed to monitor the pressure at which a user applies the tip to the subject's skin.

51. The device of claim 50, wherein the display comprises:

a first display in communication with the controller for visually indicating to a user of the device whether a pressure ulcer was detected in the measurement region; and at least one visual indicator in communication with the controller for providing feedback to the user regarding the pressure at which the user is applying the tip to the subject's skin.

52. The device of claim 51, wherein the first display further is capable of displaying an indication regarding the skin firmness and skin temperature.

53. A device for diagnosing pressure ulcers in a measurement region of a subject, the device comprising:

a tip for pressing against skin in the measurement region of the subject, wherein the tip comprises:

two or more photodetectors;

an emitter assembly, comprising two or more light sources, for emitting light energy from the tip toward the skin of the subject, wherein the two or more photodetectors sense reflected light energy that is emitted from the emitter assembly and reflected by the skin of the measurement region; and at least one pressure sensor for sensing the pressure at which the tip is applied to the skin of the subject; and a processor-based controller in communication with the two or more photodetectors and the at least one pressure sensor, wherein the controller is programmed to determine whether a pressure ulcer is present in the measurement region and, when a pressure ulcer is detected, to determine a skin layer depth of the pressure ulcer, based on input from the two or more photodetectors and the at least one pressure sensor.

54. The device of claim 53, wherein the controller is programmed to determine whether a pressure is present based on input from the photodetectors at two or more static pressure levels for the tip against the skin of the subject and transient pressure.

55. The device of claim 54, further comprising at least one user interface in communication with the controller, wherein the at least one user interface is for displaying:

an indication of whether a pressure ulcer is detected in the measurement region; and an indication of the pressure applied by the user for the tip against the skin.

56. The device of claim 55, wherein the at least one user interface provides feedback to the user regarding whether the user is applying pressure in an appropriate pressure range.

* * * * *

UNITED STATES PATENT AND TRADEMARK OFFICE
CERTIFICATE OF CORRECTION

| | | |
|---|---|---|
| PATENT NO. | : 8,116,838 B2 | Page 1 of 2 |
| APPLICATION NO. | : 12/324445 | |
| DATED | : February 14, 2012 | |
| INVENTOR(S) | : Gaspard et al. | |

It is certified that error appears in the above-identified patent and that said Letters Patent is hereby corrected as shown below:

In the Specifications

COL. 2, LINE 62

Delete "concave" and substitute therefor --convex--.

COL. 2, LINE 66

Delete ", and deoxyhemglobin" and substitute therefor --, and deoxyhemoglobin--.

COL. 4, LINE 3

Delete "deoxyhemoblobin" and substitute therefor --deoxyhemoglobin--.

COL. 4, LINE 27

Delete "The devise" and substitute therefor --The device--.

COL. 4, LINE 54

Delete "color light energy and may to" and substitute therefor --color light energy and may--.

COL. 6, LINE 40

Delete "concave" and substitute therefor --convex--.

COL. 6, LINE 43

Delete "concave" and substitute therefor --convex--.

COL. 9, LINE 39

Delete "determination of the whether there exists a PU" and substitute therefor --determination of whether there exists a PU--.

Signed and Sealed this
Twenty-fifth Day of March, 2014

Michelle K. Lee
*Deputy Director of the United States Patent and Trademark Office*

COL. 10, LINE 47

Delete "FIG. 8 provides illustrates yet another embodiment" and substitute therefor --FIG. 8 illustrates yet another embodiment--.

COL. 12, LINE 14

Delete ", when a pressure ulcer is detected, to" and substitute therefor --, when a pressure ulcer is detected to--.

In the Claims
COL. 12, LINE 18, Claim 2

Delete "concave" and substitute therefor --convex--.

COL. 12, LINE 22, Claim 3

Delete ", and deoxyhemglobin at" and substitute therefor --, and deoxyhemoglobin at--.

COL. 12, LINE 42, Claim 6

Delete "wherein the at least output indicator" and substitute therefor --wherein the at least one output indicator--.

COL. 14, LINE 14, Claim 29

Delete "concave" and substitute therefor --convex--.

COL. 14, LINE 18, Claim 30

Delete ", and deoxyhemglobin at" and substitute therefor --, and deoxyhemoglobin at--.

COL. 16, LINE 37, Claim 53

Delete ", when a pressure ulcer is detected, to" and substitute therefor --, when a pressure ulcer is detected to--.